United States Patent
Lorenzo et al.

(10) Patent No.: US 12,376,859 B2
(45) Date of Patent: Aug. 5, 2025

(54) EMBOLIC COIL PROXIMAL CONNECTING ELEMENT AND STRETCH RESISTANT FIBER

(71) Applicant: DePuy Synthes Products, Inc., Raynham, MA (US)

(72) Inventors: Juan Lorenzo, Davie, FL (US); Tyson Montidoro, Raynham, MA (US); Daniel Solaun, Miami, FL (US); David Blumenstyk, Miami, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 652 days.

(21) Appl. No.: 17/375,482

(22) Filed: Jul. 14, 2021

(65) Prior Publication Data
US 2021/0338248 A1 Nov. 4, 2021

Related U.S. Application Data

(63) Continuation-in-part of application No. 16/573,469, filed on Sep. 17, 2019, now Pat. No. 11,439,403.

(51) Int. Cl.
*A61B 17/12* (2006.01)

(52) U.S. Cl.
CPC .... *A61B 17/12113* (2013.01); *A61B 17/1215* (2013.01); *A61B 17/12154* (2013.01); *A61B 2017/1205* (2013.01)

(58) Field of Classification Search
CPC ........ A61B 17/12109; A61B 17/12113; A61B 17/1214–17/12154; A61B 2017/1205–2017/12095
See application file for complete search history.

(56) References Cited

U.S. PATENT DOCUMENTS

| 3,429,408 A | 2/1969 | Maker et al. |
| 5,108,407 A | 4/1992 | Geremia et al. |

(Continued)

FOREIGN PATENT DOCUMENTS

| EP | 1728478 A1 | 12/2006 |
| EP | 1985244 A2 | 10/2008 |

(Continued)

OTHER PUBLICATIONS

Extended European Search Report issued in European Patent Application No. 22 18 4574 dated Dec. 8, 2022.

(Continued)

*Primary Examiner* — Kathleen S Holwerda
(74) *Attorney, Agent, or Firm* — TROUTMAN PEPPER LOCKE LLP

(57) ABSTRACT

An embolic coil implant having a stretch resistant fiber therethrough and dual-functional engagement feature at its proximal end is provided. The stretch resistant fiber can be effective to limiting separation of windings of the embolic coil. The engagement feature can provide an attachment for securing the embolic coil to an engagement system of a delivery tube and for securing the stretch resistant fiber at the proximal end of the embolic coil. The engagement feature can have two engagement surfaces affixed to a proximal end of the embolic coil that are longitudinally offset from each other by a distance that is about half of a diameter of a wire of the embolic coil.

15 Claims, 12 Drawing Sheets

(56) References Cited

U.S. PATENT DOCUMENTS

| | | |
|---|---|---|
| 5,122,136 A | 6/1992 | Guglielmi et al. |
| 5,217,484 A | 6/1993 | Marks |
| 5,250,071 A | 10/1993 | Palermo |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,417,708 A | 5/1995 | Hall et al. |
| 5,484,409 A | 1/1996 | Atkinson et al. |
| 5,569,221 A | 10/1996 | Houser et al. |
| 5,582,619 A | 12/1996 | Ken |
| 5,624,449 A | 4/1997 | Pham et al. |
| 5,853,418 A | 12/1998 | Ken et al. |
| 5,899,935 A | 5/1999 | Ding |
| 5,925,059 A | 7/1999 | Palermo et al. |
| 6,113,622 A | 9/2000 | Tieshima |
| 6,203,547 B1 | 3/2001 | Nguyen et al. |
| 6,334,864 B1 | 1/2002 | Amplatz et al. |
| 6,368,338 B1 | 4/2002 | Konya et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 6,636,758 B2 | 10/2003 | Sanchez et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,708,754 B2 | 5/2010 | Balgobin et al. |
| 7,708,755 B2 | 5/2010 | Davis, III et al. |
| 7,722,636 B2 | 5/2010 | Farnan |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,942,894 B2 | 5/2011 | West |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 8,449,591 B2 | 5/2013 | Litzenberg et al. |
| 8,795,316 B2 | 8/2014 | Balgobin et al. |
| 8,974,488 B2 | 3/2015 | Tan et al. |
| 9,155,540 B2 | 10/2015 | Lorenzo |
| 9,232,992 B2 | 1/2016 | Heidner |
| 9,314,326 B2 | 4/2016 | Wallace et al. |
| 9,486,223 B2 | 11/2016 | Que et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,907,555 B2 | 3/2018 | Buiser et al. |
| 9,918,718 B2 | 3/2018 | Lorenzo |
| 10,034,670 B2 | 7/2018 | Elgård et al. |
| 10,282,851 B2 | 5/2019 | Gorochow |
| 10,285,710 B2 | 5/2019 | Lorenzo et al. |
| 10,517,604 B2 | 12/2019 | Bowman et al. |
| 10,806,402 B2 | 10/2020 | Cadieu et al. |
| 10,806,461 B2 | 10/2020 | Lorenzo |
| 10,806,462 B2 | 10/2020 | Lorenzo |
| 10,888,331 B2 | 1/2021 | Pederson et al. |
| 11,051,928 B2 | 7/2021 | Casey et al. |
| 2001/0049519 A1 | 12/2001 | Holman et al. |
| 2001/0056281 A1 | 12/2001 | Wallace et al. |
| 2002/0072705 A1 | 6/2002 | Vrba et al. |
| 2002/0165569 A1 | 11/2002 | Ramzipoor et al. |
| 2003/0216757 A1 | 11/2003 | Gerberding |
| 2004/0002731 A1 | 1/2004 | Aganon et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2005/0149108 A1 | 7/2005 | Cox |
| 2006/0025802 A1 | 2/2006 | Sowers |
| 2006/0064151 A1 | 3/2006 | Guterman |
| 2006/0111771 A1 | 5/2006 | Ton et al. |
| 2006/0116711 A1 | 6/2006 | Elliott et al. |
| 2006/0135021 A1 | 6/2006 | Calhoun et al. |
| 2006/0155303 A1 | 7/2006 | Konya et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0083132 A1 | 4/2007 | Sharrow |
| 2007/0083226 A1 | 4/2007 | Buiser et al. |
| 2007/0179520 A1 | 8/2007 | West |
| 2007/0203519 A1 | 8/2007 | Lorenzo et al. |
| 2007/0233168 A1 | 10/2007 | Davis et al. |
| 2007/0270903 A1 | 11/2007 | Davis, III et al. |
| 2007/0270930 A1 | 11/2007 | Schenck |
| 2007/0299422 A1 | 12/2007 | Inganas et al. |
| 2008/0027561 A1 | 1/2008 | Mitelberg et al. |
| 2008/0035160 A1 | 2/2008 | Woodson et al. |
| 2008/0045997 A1 | 2/2008 | Balgobin et al. |
| 2008/0082113 A1 | 4/2008 | Bishop et al. |
| 2008/0097462 A1 | 4/2008 | Mitelberg et al. |
| 2008/0119887 A1 | 5/2008 | Que et al. |
| 2008/0221654 A1 | 9/2008 | Buiser et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0036877 A1 | 2/2009 | Nardone et al. |

(56) References Cited

U.S. PATENT DOCUMENTS

| | | |
|---|---|---|
| 2009/0062726 A1 | 3/2009 | Ford et al. |
| 2009/0099592 A1 | 4/2009 | Buiser et al. |
| 2009/0177261 A1 | 7/2009 | Teoh et al. |
| 2009/0312748 A1 | 12/2009 | Johnson et al. |
| 2010/0094395 A1* | 4/2010 | Kellett ............... A61B 17/1215 623/1.11 |
| 2010/0114017 A1 | 5/2010 | Lenker et al. |
| 2010/0160944 A1 | 6/2010 | Teoh et al. |
| 2010/0324649 A1 | 12/2010 | Mattsson |
| 2011/0092997 A1 | 4/2011 | Kang |
| 2011/0295303 A1* | 12/2011 | Freudenthal ....... A61B 17/1215 606/200 |
| 2012/0035707 A1 | 2/2012 | Mitelberg et al. |
| 2012/0041472 A1 | 2/2012 | Tan et al. |
| 2012/0283768 A1 | 11/2012 | Cox et al. |
| 2013/0066413 A1 | 3/2013 | Jin et al. |
| 2013/0138136 A1 | 5/2013 | Beckham et al. |
| 2013/0338701 A1 | 12/2013 | Wilson et al. |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0207175 A1 | 7/2014 | Aggerholm |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2015/0112378 A1 | 4/2015 | Torp |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0022275 A1 | 1/2016 | Garza |
| 2016/0157869 A1 | 6/2016 | Elgård et al. |
| 2016/0228125 A1 | 8/2016 | Pederson, Jr. et al. |
| 2016/0310304 A1 | 10/2016 | Mialhe |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0135801 A1 | 5/2017 | Delaney, Jr. et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0028779 A1 | 2/2018 | von Oepen et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0325706 A1 | 11/2018 | Hebert et al. |
| 2019/0192162 A1* | 6/2019 | Lorenzo ........... A61B 17/12109 |
| 2019/0255290 A1 | 8/2019 | Snyder et al. |
| 2019/0328398 A1 | 10/2019 | Lorenzo |
| 2020/0093499 A1 | 3/2020 | Lorenzo et al. |
| 2020/0229957 A1 | 7/2020 | Bardsley et al. |
| 2021/0001082 A1 | 1/2021 | Lorenzo et al. |

FOREIGN PATENT DOCUMENTS

| | | |
|---|---|---|
| EP | 3092956 A1 | 11/2016 |
| EP | 3501427 A1 | 6/2019 |
| EP | 3760139 A2 | 1/2021 |
| JP | 2006-334408 A | 12/2006 |
| JP | 2012-000464 A | 1/2012 |
| JP | 2012-523943 A | 10/2012 |
| JP | 2013-78584 A | 5/2013 |
| JP | 2013-212372 A | 10/2013 |
| WO | WO 2012/158152 A1 | 11/2012 |

OTHER PUBLICATIONS

Extended European Search Report for European Application No. 20196478.0, mailed Jan. 25, 2021, 11 Pages.

Extended European Search Report for European Application No. 22184574.6, mailed Dec. 6, 2022, 10 pages.

English Translation of Japanese Office Action dated Feb. 20, 2024, in corresponding JP Appln. No. 2020-155306, and submitted herewith.

* cited by examiner

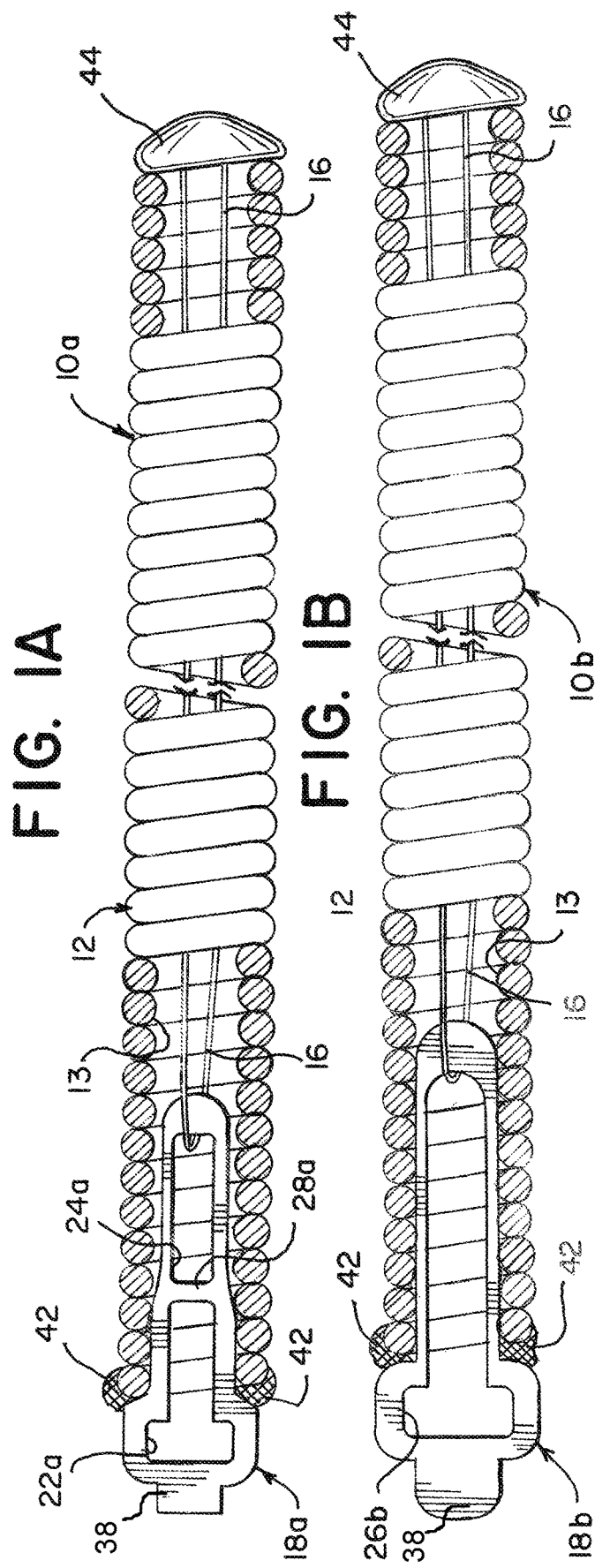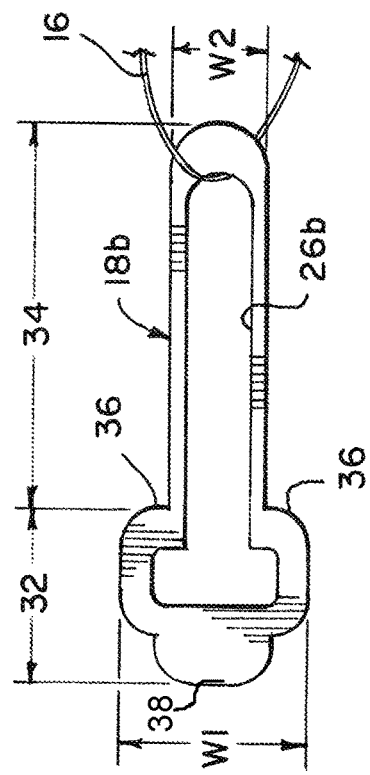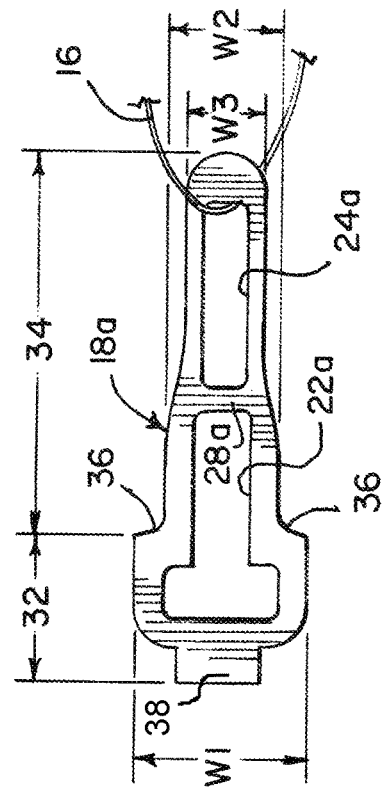

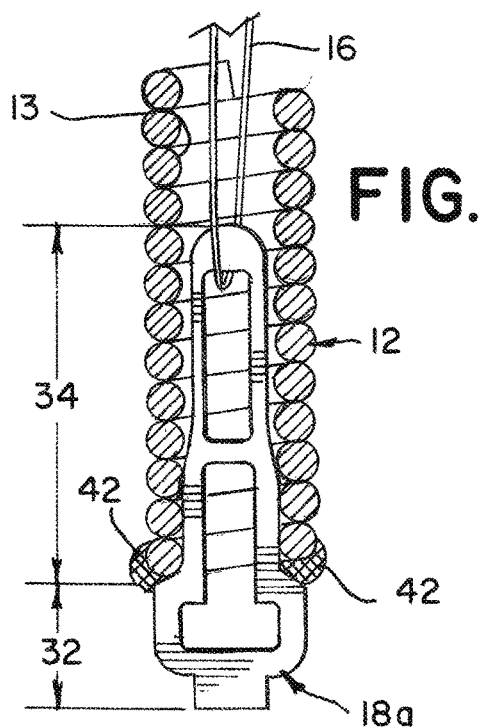
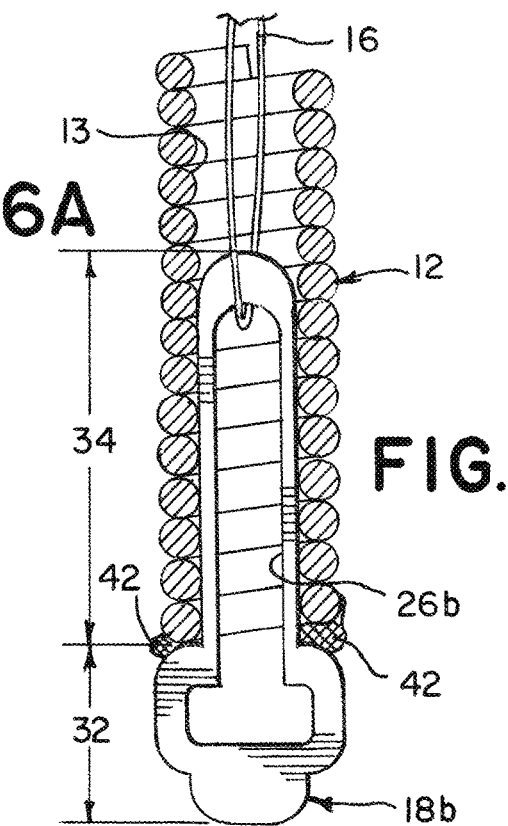
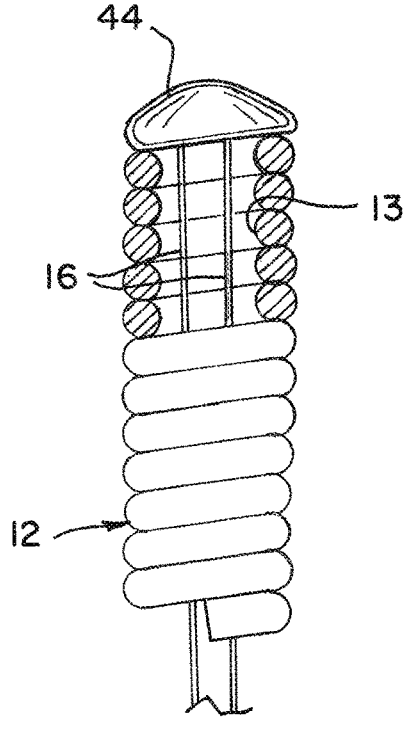
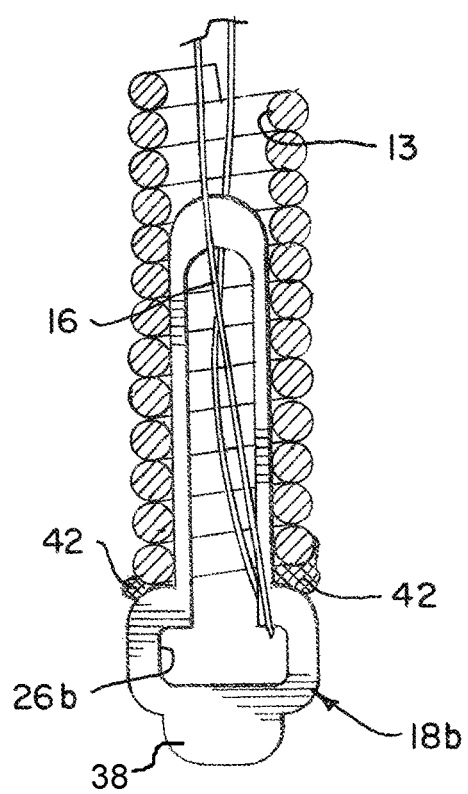

FIG. 10A
PRIOR ART
FIG. 10B
PRIOR ART
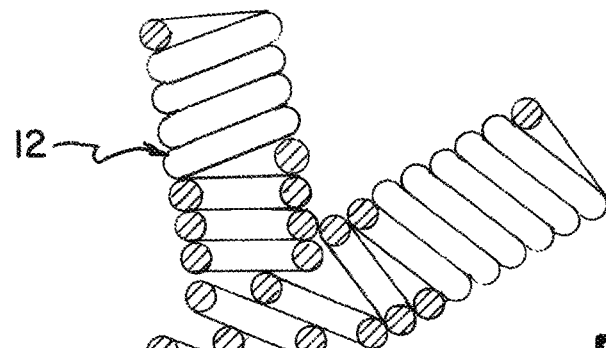
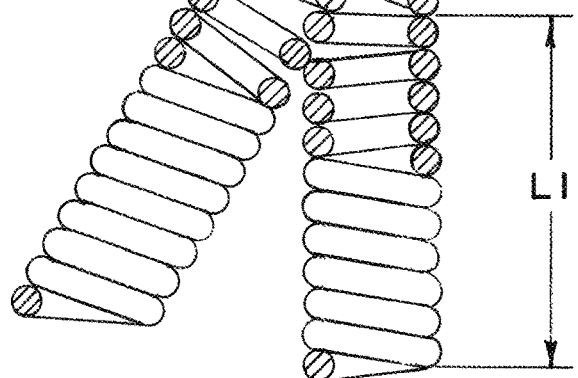
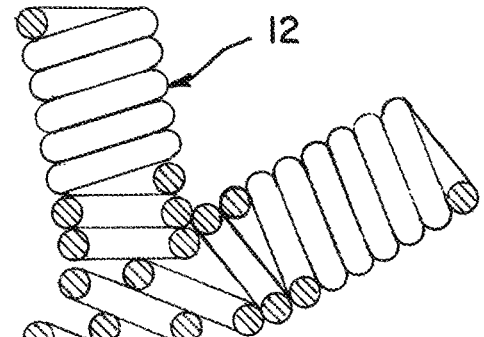
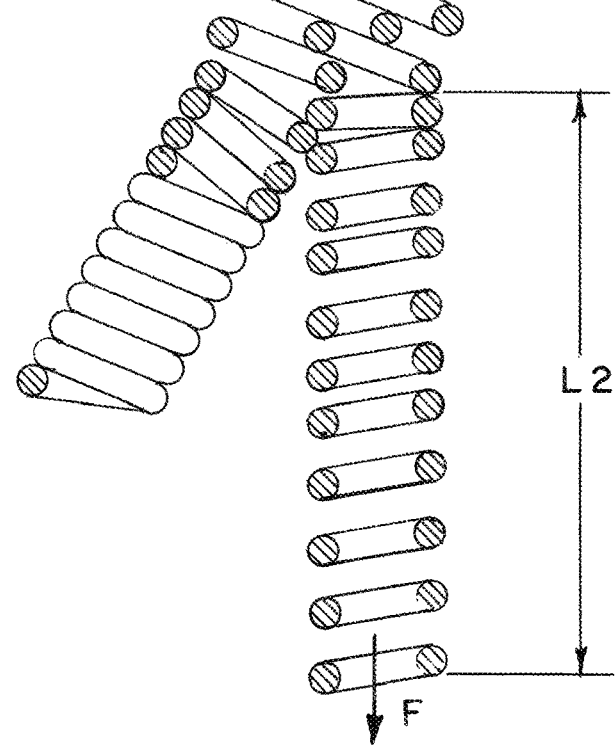

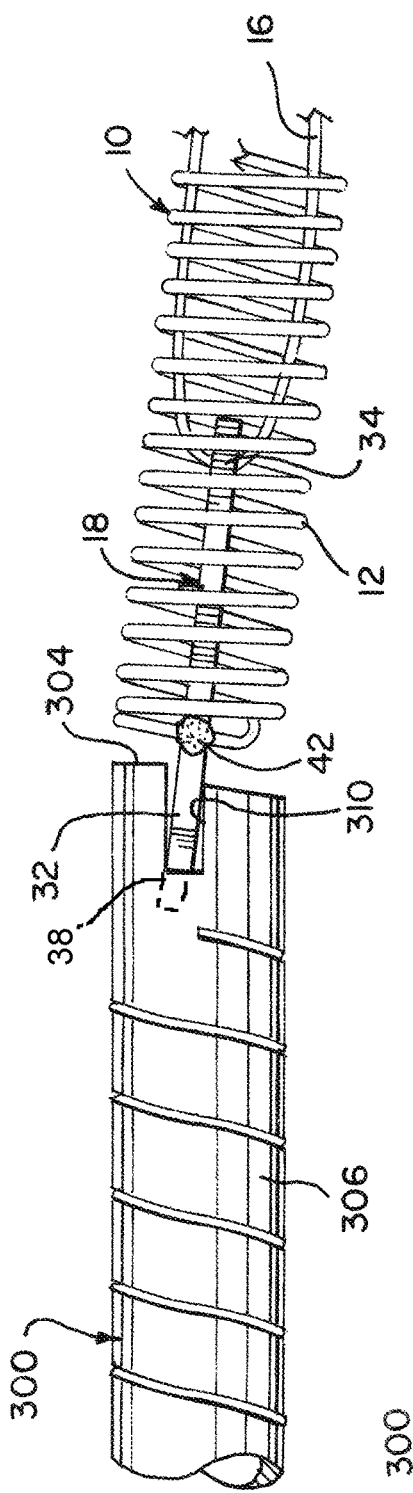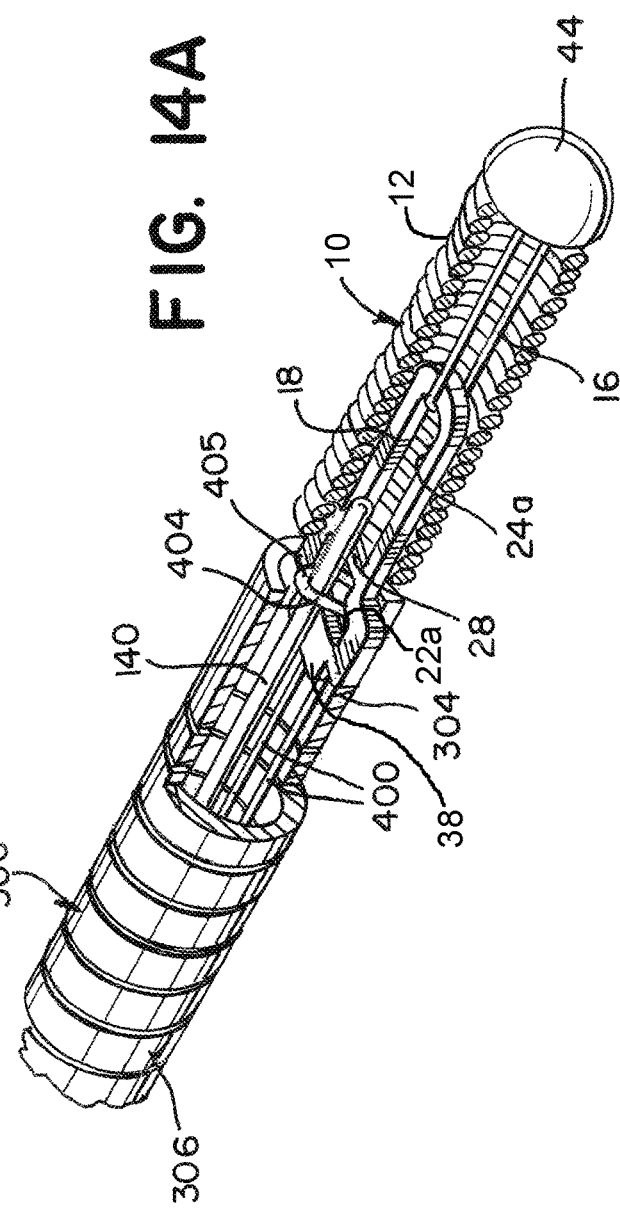

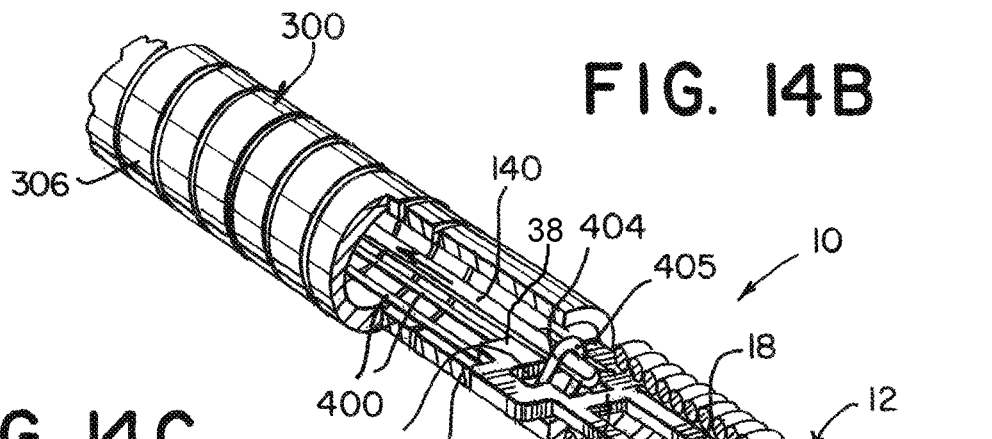
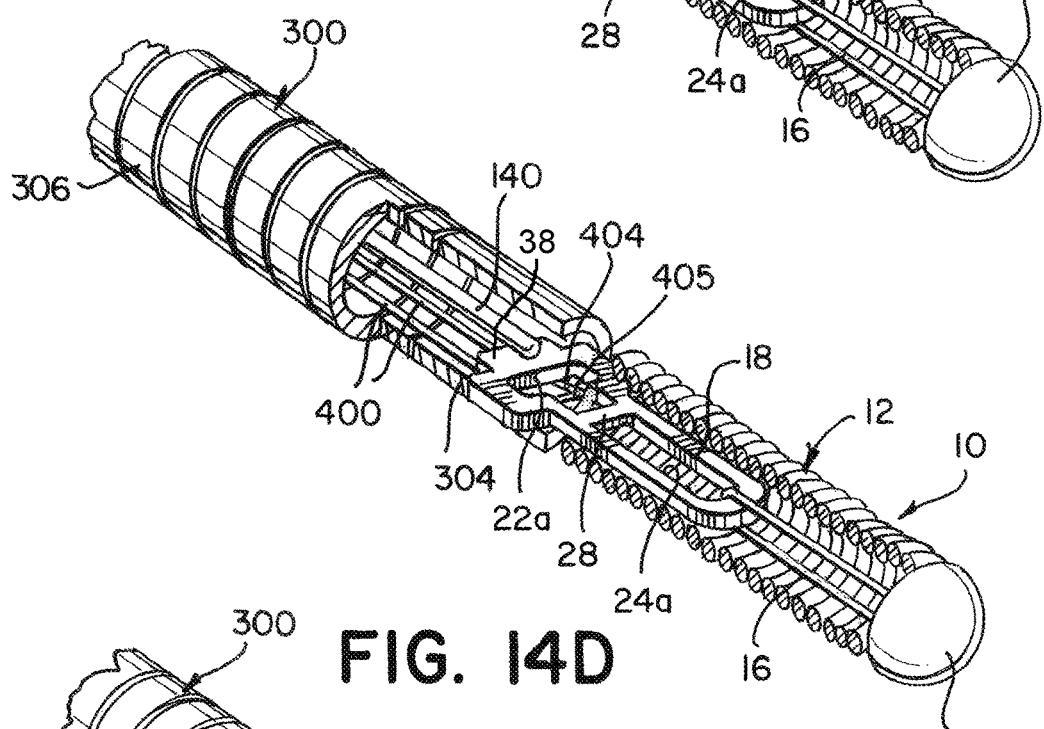
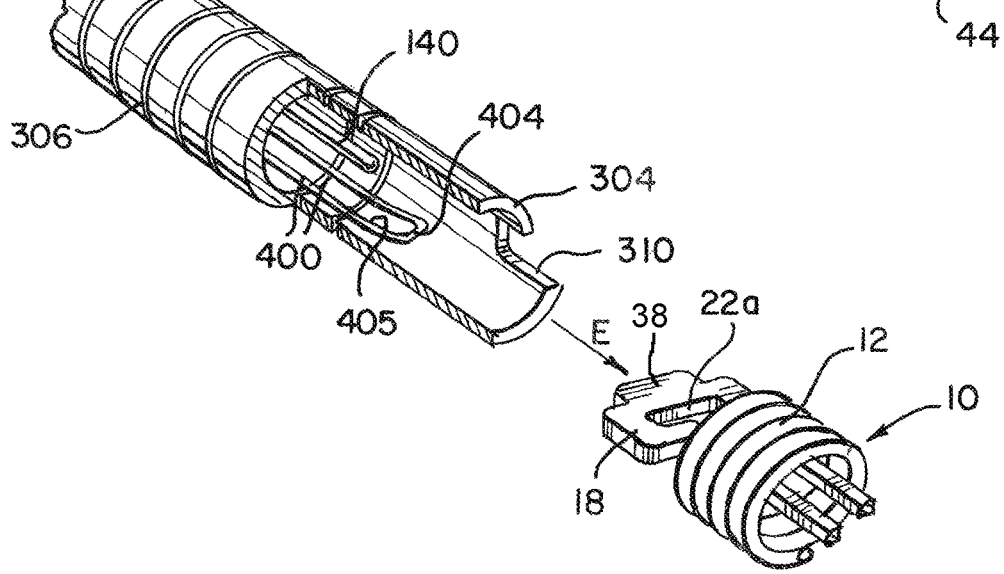

EMBOLIC COIL PROXIMAL CONNECTING ELEMENT AND STRETCH RESISTANT FIBER

CROSS REFERENCE TO RELATED APPLICATION

This application is a continuation in part to prior filed U.S. patent application Ser. No. 16/573,469 filed on Sep. 17, 2019 which is hereby incorporated by reference as set forth in full herein.

FIELD OF INVENTION

The present invention generally relates to implantable medical devices, and more particularly, to engagement features for mechanically releasably securing implantable medical devices to a delivery system.

BACKGROUND

Aneurysms can be intravascularly treated by delivering a treatment device to the aneurysm to fill the sac of the aneurysm with embolic material and/or block the neck of the aneurysm to inhibit blood flow into the aneurysm. When filling the aneurysm sac, the embolic material can promote blood clotting to create a thrombotic mass within the aneurysm. When treating the aneurysm neck without substantially filling the aneurysm sac, blood flow into the neck of the aneurysm can be inhibited to induce venous stasis in the aneurysm and facilitate natural formation of a thrombotic mass within the aneurysm.

In some current treatments, multiple embolic coils are used to either fill the aneurysm sac or treat the entrance of the aneurysm neck. A common challenge among embolic coil treatments is that implanted coils and implanted portions of partially implanted coils can become entangled and difficult to reposition. In some instances, a physician may not be able to retract a partially implanted coil and may be forced to position the coil in a non-ideal location. Improperly positioning embolic coils at the aneurysm neck can potentially have the adverse effect of impeding the flow of blood in the adjoining blood vessel, particularly if the entrance and/or sac is overpacked. If a portion of the non-ideally implanted coil becomes dislodged, it can enter the neighboring blood vessel and promote clot formation, which can ultimately lead to an obstruction that is tethered to the aneurysm and therefor extremely difficult to treat. Conversely, if the entrance and/or sac is insufficiently packed, blood flow can persist into the aneurysm.

In some current treatments, an embolic coil is attached to a tubular delivery member and delivered via a delivery catheter to an aneurysm. During delivery, the embolic coil can be engaged to the delivery member's implant engagement/deployment system (referred to herein equivalently as an "engagement system" or "deployment system"). When the embolic coil is in position, the deployment system can release the coil, the coil can be left implanted, and the delivery member can be retracted. Some treatments utilize a mechanical engagement/deployment system that can be actuated by a physician to release the implant by pulling one or more wires or other elongated members referred to generically herein as a "pull wire".

Some of the challenges that have been associated with delivering and deploying embolic coils with delivery members having mechanical engagement systems include premature release of a coil and movement of the delivery member due to push back from densely packed treatment sites.

There is therefore a need for improved methods, devices, and systems to facilitate implantation of embolic coils and other implants facing similar challenges.

SUMMARY

It is an object of the present invention to provide systems, devices, and methods to meet the above-stated needs. In some examples presented herein, separation of coil windings within an embolic coil is reduced or prevented with a stretch resistant fiber that is positioned within the lumen of the coil. Reducing or preventing the separation of coil windings can in some cases prevent an implanted portion of a partially implanted coil from being tangled with implanted coils and thereby make it possible to more easily reposition and/or extract some or all of the coil. In some examples presented herein, during delivery of the embolic coil the distal end of the pull wire is supported by an engagement/detachment feature (referred to herein equivalently as "engagement feature", "detachment feature", or "key") affixed to the proximal end of the embolic coil. The support provided by the key can in some cases reduce the likelihood that the embolic coil is prematurely released. In some examples presented herein, the embolic implant can have a highly flexible proximal portion. The flexibility of the embolic implant can in some cases reduce the force on the delivery member due to push back from densely packed treatment sites and thereby reduce movement of the delivery member due to the push back.

To meet some or all of the needs, an implant having an embolic coil, a stretch resistant fiber extended through the coil, and a detachment feature/key at the coil's proximal end is provided. The stretch resistant fiber can be effective to limit separation of windings of the embolic coil. The key can provide an attachment for securing the embolic coil to an engagement system of a delivery tube and for securing the stretch resistant fiber at the proximal end of the embolic coil.

An example method for treating an aneurysm can include one or more of the following steps presented in no particular order, and the method can include additional steps not included here. Some or all of an implant having an embolic coil and a stretch resistant fiber can be positioned within the aneurysm. A portion of the embolic coil can be retracted from the aneurysm. The portion can be inhibited from lengthening by the stretch resistant fiber when the portion is retraced from the aneurysm. The embolic coil can be bent, and the stretch resistant fiber can limit separation of the windings of the embolic coil at the bend.

The stretch resistant fiber can be positioned to extend within a lumen of the embolic coil. The stretch resistant fiber can under tension along a majority of the length of the stretch resistant fiber.

The implant can be secured to a delivery system with a key engaged to the stretch resistant fiber. To secure the implant to the delivery system, a loop wire of the delivery system can be positioned through the key, and a pull wire can be positioned through an opening in the loop wire. When the implant is secured to the delivery system, the pull wire can be supported by the key both in the proximal direction from the loop wire and the distal direction from the loop wire.

During delivery and/or positioning of the implant, the key can be visualized radiographically.

The key can be released from the delivery system, thereby releasing the implant from the delivery system. When the implant is released, the key can remain attached to the implant.

An example embolic implant can include an embolic coil, a detachment feature, and a stretch resistant fiber. The detachment feature can be affixed to the embolic coil at the proximal end of the embolic coil. The stretch resistant fiber can be engaged to the detachment feature, extend through the lumen of the embolic coil, and can be affixed to the embolic coil at the distal end of the embolic coil. Configured thusly, the stretch resistant fiber can be effective to limit separation of windings of the embolic coil as the embolic coil is reshaped.

The stretch resistant fiber can be a suture. The stretch resistant fiber can be inelastic.

The detachment feature can be radiopaque.

The detachment feature can have an opening through which the stretch resistant fiber passes. The opening can extend proximally from a proximal end of the embolic coil.

The detachment feature can have a singular opening that is sized to receive a loop wire of a mechanical delivery system and through which the stretch resistant fiber passes.

Alternatively, the detachment feature can have two separate openings: a first opening through which the stretch resistant fiber passes and a second opening sized to receive a loop wire of a mechanical delivery system. The first opening can be at least partially positioned within the lumen of the embolic coil. The second opening can be at least partially positioned in the proximal direction from the proximal end of the embolic coil.

An example system can include the example embolic implant having the detachment feature with two separate openings and a mechanical delivery system including a loop wire and a pull wire. The stretch resistant fiber can pass through one of the two openings, and the loop wire can pass through the other of the two openings. The pull wire can be positioned through an opening in the loop wire, thereby securing the implant to the mechanical delivery system with the loop wire. The detachment feature can further include a bridge positioned between the two openings of the detachment feature, and the bridge can support a portion of the pull wire that is in the distal direction from the loop opening in the loop wire.

The detachment feature can have a proximal portion disposed proximally from the lumen of the embolic coil and a distal portion disposed within the lumen. The proximal portion can have a width that measures greater than the inner diameter of the embolic coil lumen, and the distal portion can have a width that measures about equal to the inner diameter of the embolic coil lumen.

An example method for constructing or designing an embolic implant such as an example implant as described herein can include one or more of the following steps presented in no particular order, and the method can include additional steps not included here. A detachment feature can be cut from a flat sheet material. One or more openings can be cut from the detachment feature. A stretch resistant fiber can be threaded through an opening in the detachment feature. The stretch resistant fiber can be extended through a lumen of an embolic coil. The detachment feature can be affixed at one end of the embolic coil. The stretch resistant fiber can be affixed at the other end of the embolic coil. Tension can be provided along the stretch resistant fiber between the detachment feature and the second end of the embolic coil.

A portion of a mechanical deployment system can be extended through an opening in the detachment feature to engage the detachment feature to a delivery tube. The mechanical deployment system can be extended through the same opening through which the stretch resistant fiber is threaded or an opening in the detachment feature that is separate from the opening through which the stretch resistant fiber is threaded.

The detachment feature can be cut from a radiopaque flat sheet material.

A distal portion of the detachment feature can be inserted within the lumen of the embolic coil and a proximal portion of the detachment feature can be extended proximally from the proximal end of the embolic coil. The embolic coil and the detachment feature can be selected such that the proximal portion of the detachment feature is wider than the inner diameter of the embolic coil's lumen and the distal portion of the detachment feature is about equal to the inner diameter of the embolic coil's lumen.

To affix the detachment feature to the embolic coil, the detachment feature can be welded to the embolic coil.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 1A and 1B are illustrations of embolic implants according to aspects of the present invention;

FIGS. 2A and 2B are illustrations of detachment features each having a stretch resistant fiber therethrough according to aspects of the present invention;

FIGS. 6A and 6B are illustrations of detachment features affixed to an embolic coil according to aspects of the present invention;

FIG. 7 is an illustration of the stretch resistant fiber affixed to an end of the embolic coil according to aspects of the present invention;

FIGS. 8A through 8C illustrate a time sequence wherein an embolic coil stretches as a result of a non-optimal stretch resistant fiber placement;

FIG. 10A is an illustration of embolic coils becoming tangled, and

FIG. 10B is an illustration of a tangled coil becoming elongated as illustrations of a problem with the prior art;

FIG. 13 is an illustration of an embolic implant secured to a delivery tube according to aspects of the present invention;

FIGS. 14A through 14D illustrate a sequence of steps for releasing an embolic implant from a delivery tube according to aspects of the present invention;

DETAILED DESCRIPTION

Figure 3:
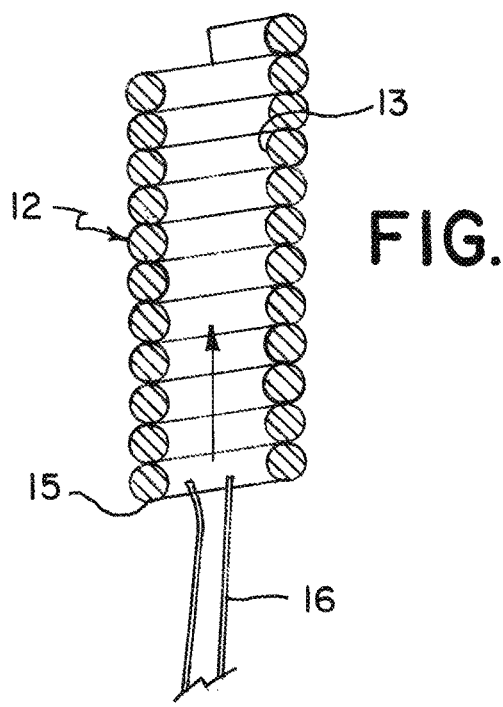
FIG. 3 is an illustration of a stretch resistant fiber being inserted into a lumen of an embolic coil according to aspects of the present invention.

An object of the present invention is to attain more precise and repeatable implant detachment. More specifically, it is an object of the present invention to facilitate implantation of embolic coils and other implants facing challenges such as partially implanted implants becoming difficult to reposition, delivery systems shifting position due to push back during implantation, and/or implants releasing prematurely. To meet some or all of these needs, example implants can include a stretch resistant fiber to limit stretching and other deformation of the embolic portion (e.g. embolic coil) of the implant and a detachment feature to which the stretch resistant fiber can be secured and to which a delivery system can detachably attach.

To facilitate repositioning of the implant, the stretch resistant fiber can extend through the embolic coil and limit separation of windings of the coil when the coil is bent and pulled. By limiting the separation of the windings, the embolic coil is less likely to become tangled when partially implanted and less likely to be stretched or otherwise deformed when retracted when partially implanted. The embolic coil can thereby be more easily repositioned. In some examples, the detachment feature can include two separate openings, one for securing the stretch resistant fiber, and another for being engaged to an engagement system. The dual opening detachment feature can reduce potential manufacturing challenges to provide for reliable stretch resistant fiber positioning and therefore more reliably provide implants that can be more easily repositioned.

To reduce effects of push back during implantation, the detachment feature can be sized and affixed to the embolic coil to provide an embolic coil implant with a highly flexible proximal section. An embolic coil implant having a highly flexible proximal section can reduce push back force on the delivery tube and thereby mitigate the effects of the delivery tube shifting. Additionally, or alternatively, the detachment feature can be sized to mate with a delivery tube having a highly flexible distal section, and the highly flexible distal section of the delivery tube can mitigate the effects of the delivery tube shifting. When an embolic coil implant having a highly flexible proximal section is mated to a delivery tube having a highly flexible distal portion, the combination of the flexible distal section of the delivery tube and the flexible proximal section of the implant can further mitigate the effects of delivery tube shifting.

To reduce instances of premature deployment, the detachment feature can include a bridge to support a pull wire. The detachment feature can be detachably attached to a mechanical engagement/deployment system on a delivery tube. The detachment feature can include an opening through which a loop wire of a mechanical engagement system can pass. In some examples, the detachment feature can further include a bridge positioned distally from the opening on which a distal portion of the pull wire can rest. The bridge can inhibit the pull wire from deforming due to the engagement with the loop wire and can therefore reduce the likelihood that the implant is prematurely released due to bending of the pull wire.

FIG. 1A is an illustration of an implant 10a including an embolic coil 12 with a lumen 13 therethrough, a detachment feature 18a, and a stretch resistant fiber 16. Portions of the coil 12 and welds 42 as illustrated in a cut-away view for the purposes of illustration. The detachment feature 18a can partially be positioned within the lumen 13 of the coil 12 and can extend out of the coil 12. The detachment feature 18a can include a distal opening 24a through which the stretch resistant wire 16 is looped, and a proximal opening 22a sized to receive a loop wire or other engagement mechanism of a mechanical implant engagement system. The detachment feature 18a can include a bridge 28a positioned between the distal opening 24a and the proximal opening 22a. The detachment feature 18a can include a proximal tab 38 sized to fit within a lumen of a delivery tube. The stretch resistant fiber 16 can be secured at an end of the embolic coil 12 opposite the end to which the detachment feature 18a is attached with a weld 44 or other appropriate attachment.

The detachment feature 18a can be tapered as it extends further within the lumen 13 of the embolic coil 12 to allow the embolic coil 12 to have additional flexibility where the embolic coil 12 surrounds the tapered region. The detachment feature 18a can also have a substantially flat profile, providing even greater flexibility in directions into and out of the plane of the image.

The detachment feature 18a can be sufficiently secured with attachments 42 to the coil 12 without fusing any windings of the coil 12 (as illustrated) or by fusing a small number of windings (e.g. 5 or fewer windings). Compared to known solutions wherein typically ten or more windings are soldered together (with limited control over the number of fused windings), the attachments 42 to the coil 12 can be realized with significantly fewer fused coil windings. By reducing the number of windings that are fused, the proximal section of the implant 10a can have increased flexibility compared to known designs which rely on fusing windings from the proximal end of the embolic coil.

FIG. 1B is an illustration of an alternatively constructed implant 10b having elements as described in relation to FIG. 1A with like reference numbers indicating like elements. Portions of the coil 12 and welds 42 as illustrated in a cut-away view for the purposes of illustration. Compared to the implant 10a illustrated in FIG. 1A, the implant 10b can have an alternative detachment feature 18b having a single opening 26b that provides an opening to which a mechanical engagement system can engage and through which the stretch resistant fiber 16 can be looped. The detachment feature 18b illustrated in FIG. 1B also lacks the extended tapered region of the detachment feature 18a illustrated in FIG. 1A. Although the tapered region of the detachment feature 18a illustrated in FIG. 1A can provide for a more flexible proximal section of the implant 10a compared to the implant 10b in FIG. 1B, the detachment feature 18b illustrated in FIG. 1B can nevertheless provide greater flexibility over known embolic coil implants by providing flexibility in directions into and out of the plane of the image by virtue of being flat and provide increased flexibility over designs which rely on fusing windings from the proximal end of the embolic coil by virtue of the low profile attachments 42.

FIGS. 2A and 2B through FIG. 7 illustrate a sequence of steps for constructing the implants 10a and 10b illustrated in FIGS. 1A and 1B. FIGS. 2A and 2B illustrate the stretch resistant fiber 16 being passed through the detachment features 18a, 18b. The detachment features 18a, 18b can be laser cut from a flat sheet material. The flat sheet material is preferably a radiopaque material that can be welded or otherwise affixed to the embolic coil 12.

FIG. 2A illustrates the dual opening detachment feature 18a having a proximal portion 32 that is sized to engage a mechanical engagement system and/or delivery tube. The proximal portion 32 is illustrated as having a width W1. The dual opening detachment feature 18a can have a distal portion 34 that is sized to fit within the lumen 13 of the embolic coil. The distal portion 34 can have a wider section having a width W2 that is about as wide as the inner diameter of the embolic coil 12 and a tapered section having a width W3 that is significantly narrower than the inner diameter of the embolic coil 12. The detachment feature 18a can have a proximal tab 38 that is narrower than the proximal portion 32 and is sized to fit within a lumen of a delivery tube.

FIG. 2B illustrates a single opening detachment feature 18b having a proximal portion 32 that is sized to engage a mechanical engagement system and/or delivery tube. The proximal portion 32 is illustrated having a width W1. The single opening detachment feature 18b can have a distal portion 34b narrower than the proximal portion 32 and sized to fit within the lumen 13 of the coil 12. The single opening detachment feature 18b can have a proximal tab 38 that is narrower than the proximal portion 32 and sized to fit within a lumen of a delivery tube.

After the detachment feature 18a, 18b is formed, the stretch resistant fiber 16 can be threaded through the distal opening 24a of the dual opening detachment feature 18a or the single opening 26b of the single opening detachment feature 18b.

FIG. 3 is an illustration of the free ends of the stretch resistant fiber 16 being inserted into the proximal end 15 of the embolic coil 12. At the step illustrated in FIG. 3, the stretch resistant fiber 16 can be looped through a detachment feature 10a, 10b such as illustrated in FIGS. 2A and 2B.

Figure 4:
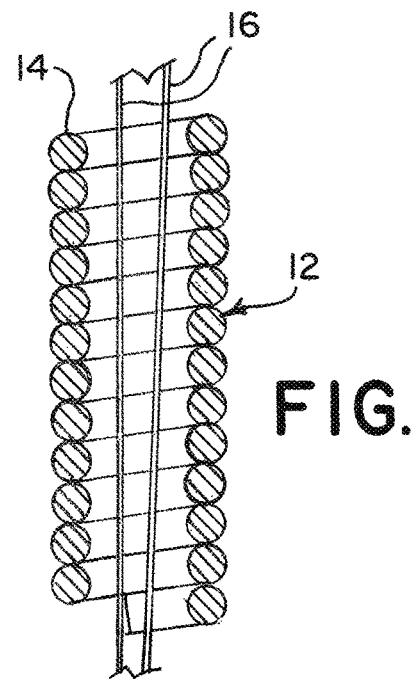
FIG. 4 is an illustration of a stretch resistant fiber exiting a lumen of an embolic coil according to aspects of the present invention.

FIG. 4 is an illustration of the free ends of the stretch resistant fiber 16 exiting the lumen 13 of an embolic coil 12 at the distal end 14 of the embolic coil 12.

Figure 5A:
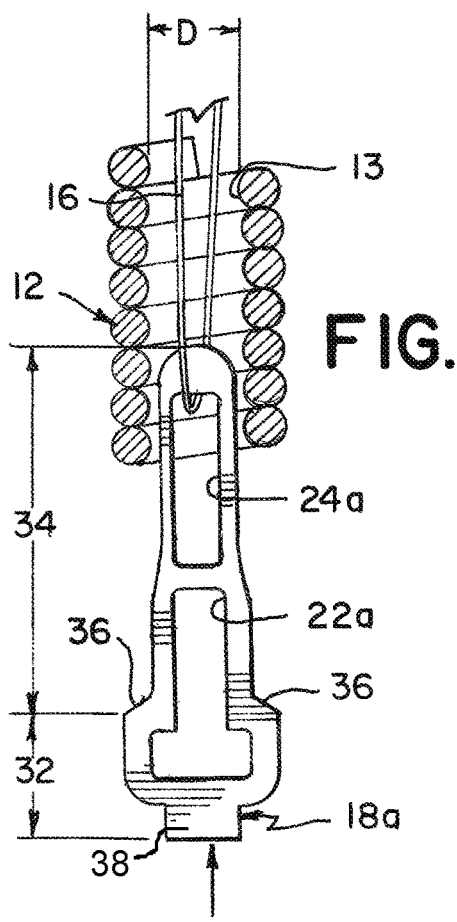
FIGS. 5A and 5B are illustrations of detachment features being inserted into a lumen of an embolic coil according to aspects of the present invention.
Figure 5B:
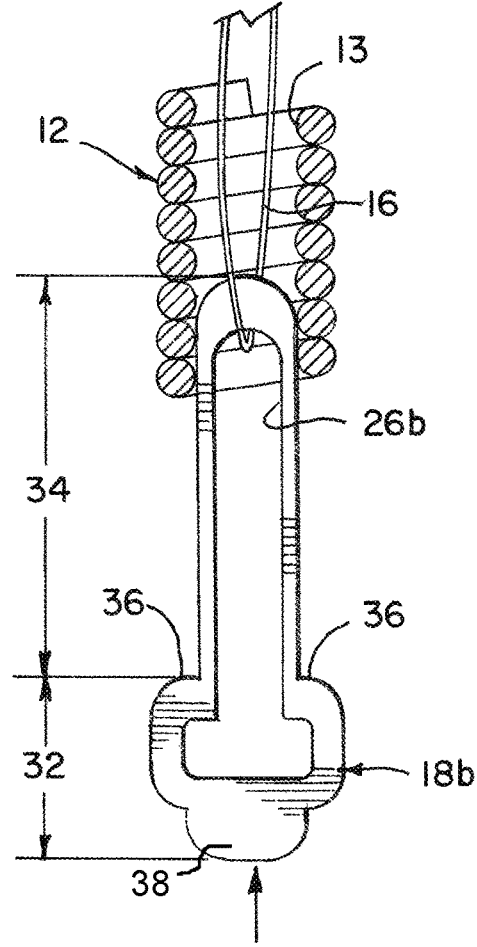

FIGS. 5A and 5B are illustrations of detachment features 18a, 18b being inserted into the lumen 13 of an embolic coil 12. After exiting the distal end 14 of the embolic coil 12, the free ends of the stretch resistant fiber 16 can be further pulled as indicated by the arrow in FIG. 4 to move the detachment feature 18a, 18b into the lumen 13 of the embolic coil 12 at the proximal end 15 of the embolic coil 12 as illustrated in FIGS. 5A and 5B and as indicated by the arrows. Before entry of the detachment feature 18a, 18b into the lumen 13 of the embolic coil 12, the embolic coil can have an inner diameter D as indicated in FIG. 5A. The proximal portion 34 of the detachment feature 18a, 18b can be sized to have a width over at least a portion of the distal portion 34 that is about equal to the inner diameter D for a snug fit. Alternatively, or additionally, at least a portion of the distal portion 34 can have a width that is larger than the diameter D to create an interference fit. Alternatively, or additionally, at least a portion of the distal portion 34 can have a width that is smaller than the diameter D to allow for greater flexibility of the coil 12 near the proximal end 15 of the coil 12.

FIGS. 6A and 6B are illustrations of the detachment features 10a, 10b with the distal portion 34 fully inserted into the lumen 13 of the embolic coil 12 and the detachment feature 18a, 18b affixed to the embolic coil 12 with welds 42 or other attachment. In both FIGS. 6A and 6B, the detachment feature 18a, 18b is illustrated having a distal portion 34 that has a width over at least a portion of the length of the distal portion 34 that is about equal to the inner diameter D of the lumen 13 of the embolic coil 12.

FIG. 7 is an illustration of the stretch resistant fiber 16 affixed to the distal end of the embolic coil 12. After affixing the detachment feature 18a, 18b, or at least positioning the detachment feature 18a to 18b as illustrated in FIGS. 6A and 6B, the stretch resistant fiber 16 can be pulled tight to reduce slack in the fiber 16 and/or create tension in the fiber 16, and the fiber 16 can be affixed with a weld 44 or other attachment. After the fiber 16 is attached, the fiber can be substantially stretch resistant as to resist significant elongation due to forces applied to the embolic coil 12 during preparation for treatment, during delivery of the implant 10a, 10b, during positioning of the implant in a treatment site, during retraction of the implant, and during deployment of the implant. In other words, the stretch resistant fiber 16 can be effective to limit lengthening of the embolic coil 12 when the embolic coil 12 is retracted from an aneurysm, and the stretch resistant fiber 16 can be effective to limit separation of the windings within the embolic coil 12 when the embolic coil 12 is bent.

Figure 8B:
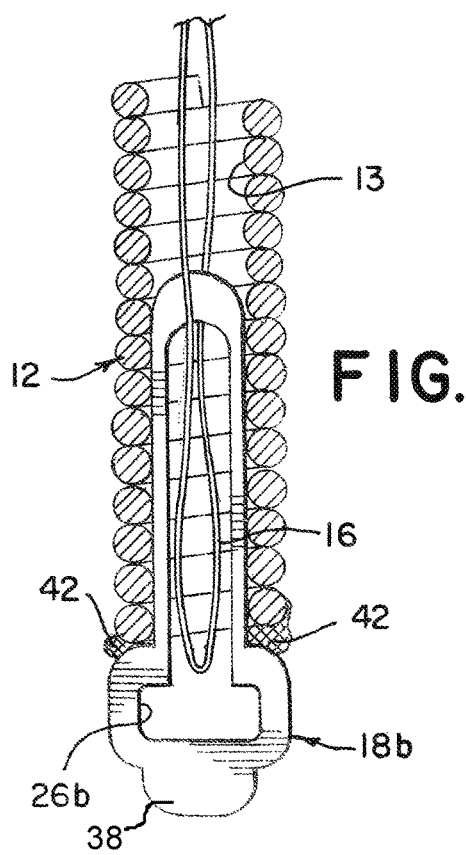
Figure 8C:
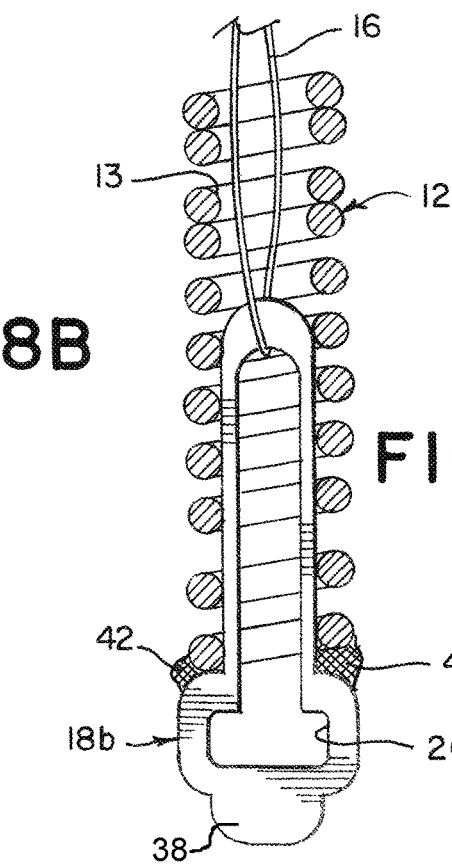

FIGS. 8A through 8C illustrate a time sequence wherein the embolic coil 12 is allowed to stretch as a result of a non-optimal stretch resistant fiber 16 placement. FIG. 8A illustrates a non-optimal fiber 16 placement within the single opening detachment feature 18b. The fiber 16 can become looped over a section of the detachment feature 18b that is not optimal such that movement of the fiber 16 as illustrated in FIG. 8B can cause the fiber 16 to disengage from the non-optimal position, and as illustrated in FIG. 8C, can allow the embolic coil 12 to stretch at least until the fiber 16 again becomes engaged to the detachment feature 18a. A manufacturing challenge is therefore to prevent the fiber 16 from being positioned at a non-optimal location such as illustrated in FIG. 8A when the attachment step illustrated in FIG. 7 is performed. If, after manufacturing is complete, the fiber 16 becomes dislodged from the non-optimal location as illustrated in FIG. 8B, when the implant 10b is manipulated, such as while being repositioned during a treatment, the embolic coil 12 can elongate as illustrated in FIG. 8C or otherwise deform.

An advantage of the dual opening detachment feature 18a is that the stretch resistant fiber 16 is less likely to become looped over a non-optimal section of the detachment feature 18a during manufacturing of the implant 10a illustrated in FIG. 1A.

Figure 9:
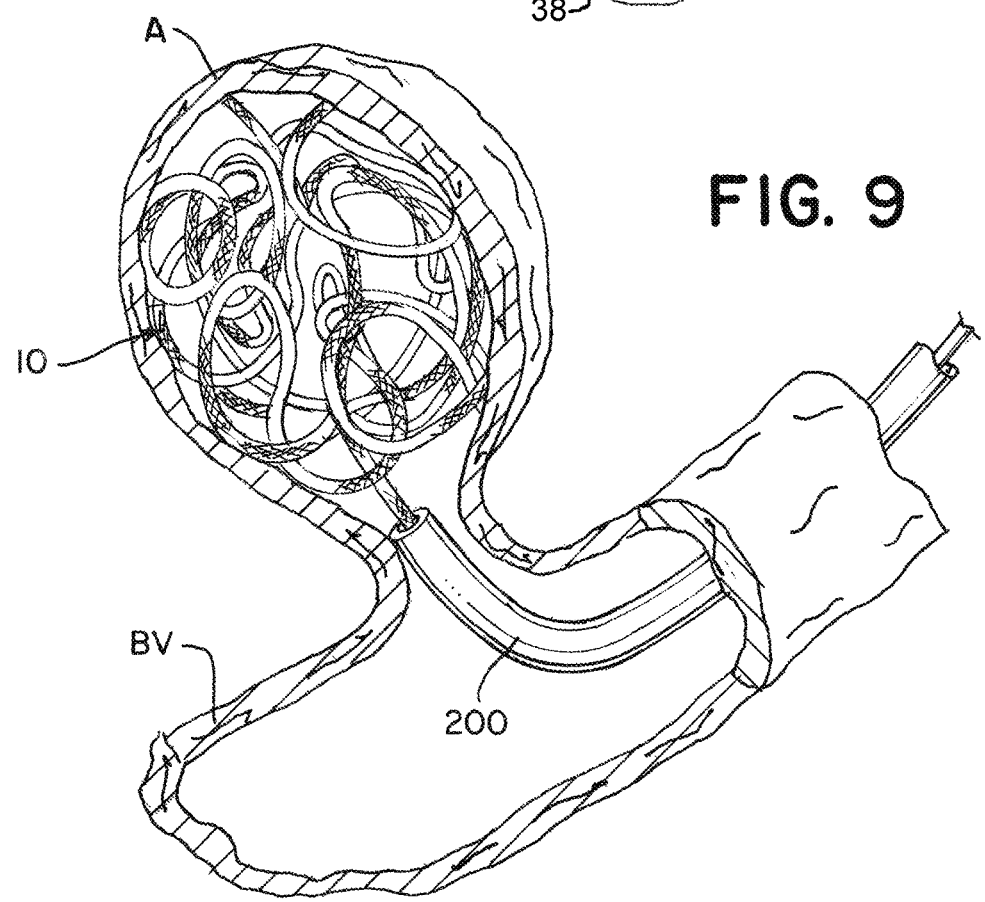
FIG. 9 is an illustration of embolic coils being positioned within an aneurysm according to aspects of the present invention.

FIG. 9 is an illustration of embolic implant(s) 10 being delivered through a delivery catheter 200 and positioned within an aneurysm A on a blood vessel BV. The implant(s) can loop and bend within the aneurysm sac to form a thrombotic mass. The implant(s) can loop back on themselves and/or loop next to other implants. As the aneurysm A becomes increasingly packed, overlapping portions of the implant 10 can press into each other.

FIG. 10A is an illustration of embolic coils 12 that lack a stretch resistant fiber 16 becoming tangled as overlapping portions of the coils press into each other. This entanglement can make it difficult or impossible for either of the coils 12 to be repositioned, which is a known problem with some current embolic coil implants. FIG. 10B illustrates a portion of the embolic coil 12 becoming elongated to a length L2 that is longer than the length L1 of that section illustrated in FIG. 10A due to a force F. FIG. 10B illustrates a scenario wherein a physician may try to attempt to retract a tangled partially implanted embolic coil and may be not only unable to retract the coil but also exacerbate the already challenging treatment by now having to position the deformed elongated coil. Entanglement can become more likely when the windings of the embolic coil are separated, for example due to bending, or when the coils are more tightly pressed together due to dense packing.

Figure 11:
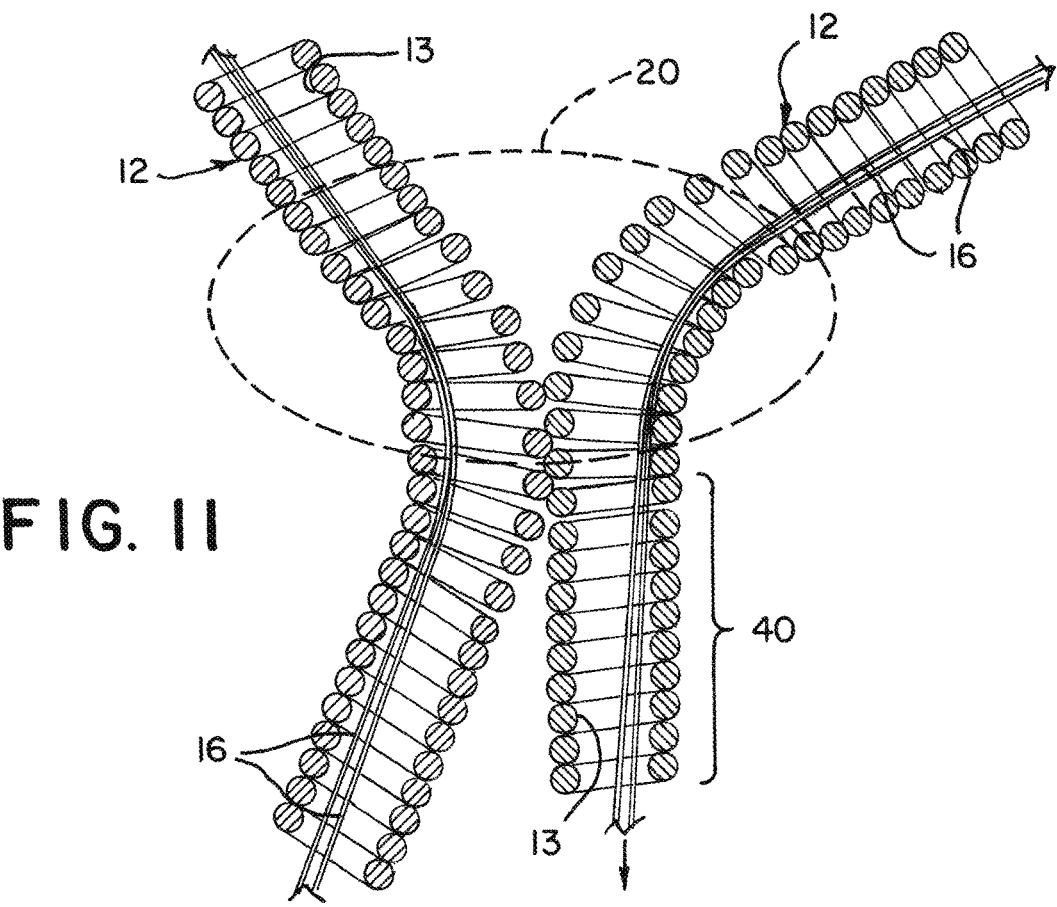
FIG. 11 is an illustration of a stretch resistant fiber inhibiting tangling and elongating of an embolic coil according to aspects of the present invention.

FIG. 11 is an illustration of example embolic coils 12 each having a stretch resistant fiber 16 being prevented from tangling and from elongating according to an aspect of the present invention. Each coil 12 is illustrated as having a bent portion 20. The stretch resistant fiber 16 can shift within the lumen 13 of each coil to allow the coil 12 to flex and bend as needed when implanted. The fiber 16 can have sufficient tension to limit the amount of separation between windings in the bent portions 20. The separation of the winds can be so limited as to inhibit the windings of two adjacent coils 12 from becoming entangled as illustrated in FIG. 10A. FIG. 11 also illustrates the force F applied to a portion 40 of the coil 12 and the portion 40 being inhibited from elongating due to tension in the stretch resistant fiber 16. FIG. 11 illustrates a scenario wherein a physician may successfully retract a partially implanted embolic coil 12 having a stretch resistant fiber 16 therethrough.

Figure 12:
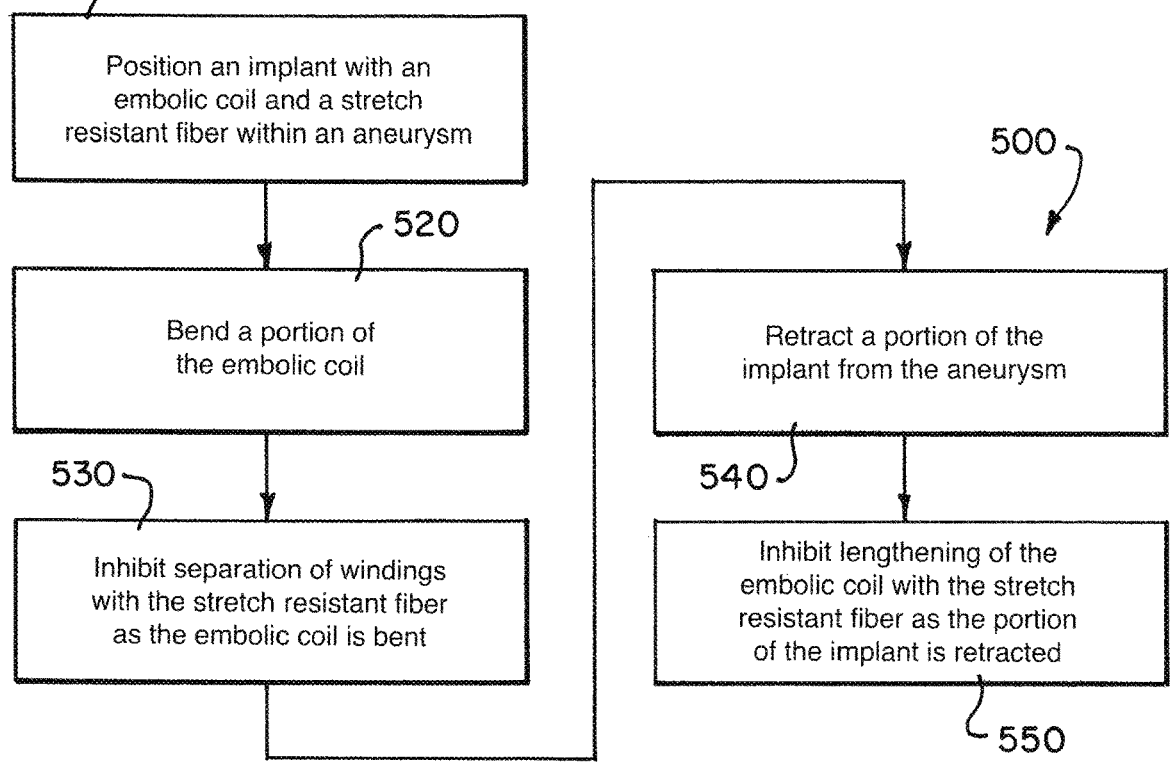
FIG. 12 is a flow diagram outlining method steps that can be conducted as part of an aneurysm treatment according to aspects of the present invention.

FIG. 12 is a flow diagram illustrating a method 500 including steps that can be conducted as part of an aneurysm treatment using an example implant 10, 10a, 10b such as described herein. In step 510, an implant having an embolic coil and stretch resistant fiber can be positioned at least partially within an aneurysm sac. In step 520, a portion of the embolic coil can be bent. In step 530, as the coil is bent, the stretch resistant fiber can inhibit separation of windings within the bent portion of the embolic coil. In step 540, some or all of the implanted portion of the implant can be retracted from the aneurysm. In step 550, as the implant is retracted, the stretch resistant fiber can inhibit lengthening of the embolic coil.

FIG. 13 is an illustration of an example embolic implant 10 such as either implant 10a, 10b illustrated in FIGS. 1A and 1B or otherwise described herein secured to a delivery tube 300. Example delivery tubes and engagement/deployment systems are described in U.S. Pat. Nos. 10,806,461 and 10,806,462 each incorporated herein by reference. The delivery tube 300 can include a notch 310 sized to receive the proximal portion 32 of the detachment feature 18 of the implant 10, and likewise the proximal portion 32 of the detachment feature 18 can be sized to fit within the notch 310 of the delivery tube 300. FIG. 13 illustrates a side view of the implant 10 highlighting the flat profile of the detachment feature 18. As described in relation to FIGS. 1A and 1B, the implant 10 can have a highly flexible proximal section by virtue of the detachment feature 18 being flat and/or by virtue of the detachment feature 18 being secured to the coil 12 without fusing several coil windings. The detachment feature 18 can also be tapered for increased flexibility in directions into and out of the plane of the image. The detachment feature 18 can further include a proximal tab 38 positioned within the lumen of the delivery tube 300.

During an aneurysm occlusion treatment, lack of flexibility of the proximal section of known embolic implants and/or lack of flexibility of a distal portion of a delivery tube can cause the delivery tube to pull back from the treatment site or otherwise move out of position while the implant is being placed in the aneurysm. A delivery tube having a more flexible distal portion and an implant having a more flexible proximal section, alone or in combination, can therefore provide a more stable system for delivering the implant. Flexible structures, however, can tend deform or expand when manipulated. The stretch resistant fiber 16 and/or detachment feature 18 alone or in combination can support the coil 12 and inhibit deformation and expansion of the coil 12 according to the principles described herein. An object of the present invention is to provide an implant 10 having a highly flexible proximal section and/or configured to mate with a delivery tube 300 having a highly flexible distal portion.

FIG. 14A is an illustration of the implant 10 and delivery tube 300 configured for delivery and positioning of the implant 10. FIGS. 14B through 14D are illustrations of a sequence of steps for releasing the example embolic implant 10 from the delivery tube 300. A portion of the delivery tube 300 is cut away for illustration purposes.

FIG. 14A illustrates the engagement system including a pull wire 140 and a loop wire 400 locked into the detachment feature 18 of the implant 12. The delivery tube 300 can include a compressible portion 306 that can be compressed. The loop wire 400 can have an opening 405 at a distal end 404 of the loop wire 400, and the opening 405 can be placed through an opening 22a in the detachment feature 18. When the pull wire 140 is put through the opening 405 the implant 12 is now secure.

The detachment feature 18 can include a bridge 28 positioned distally from the loop wire opening 405 and positioned to support a distal portion of the pull wire 140 that is distal of where the loop wire opening 405 is supported by the pull wire 140. Configured thusly, the bridge 28 can support the distal portion of the pull wire 140 such that when the loop wire 400 tugs on the pull wire 140 at the loop opening 405, the bridge 28 can inhibit the distal portion of the pull wire 140 from deforming. The proximal tab 38 can positioned to support a portion of the pull wire 140 that is proximal of where the loop wire opening 405 is supported by the pull wire 140. The combination of the bridge 28 and the proximal tab 38 can inhibit the pull wire 140 from deforming due to forces applied by the loop wire 400. The delivery tube 300 can be detachably attached to the implant 10 as illustrated in FIG. 14A during delivery of the implant 10 through the vasculature and while the implant 10 is being positioned at a treatment site. The bridge 28 can reduce the likelihood that the implant 10 is prematurely released due to bending of the pull wire 140 due to forces from the loop wire 400.

The bridge 28 can separate a proximal opening 22a and a distal opening 24a in a dual opening implant as illustrated. It is also contemplated that a single opening implant can be adapted to include a structure that can function to support the distal portion of the pull wire 140 similar to as described in relation to the illustrated bridge 28. Alternative bridge structures are therefore intended to be within the scope of the present invention.

FIG. 14B illustrates the pull wire 140 being drawn proximally to begin the release sequence for the implant 10. FIG. 14C illustrates the instant the pull wire 140 exits the opening 405 and is pulled free of the loop wire 400. The distal end 404 of the loop wire 400 falls away and exits the locking portion 18. As can be seen, there is now nothing holding the implant 10 to the delivery tube 300. FIG. 14D illustrates the end of the release sequence. Here, the compressible portion 306 has expanded/returned to its original shape and "sprung" forward. An elastic force E is imparted by the distal end 304 of the delivery tube 300 to the medical device 10 to "push" it away to ensure a clean separation and delivery of the medical device 10.

Figure 15:
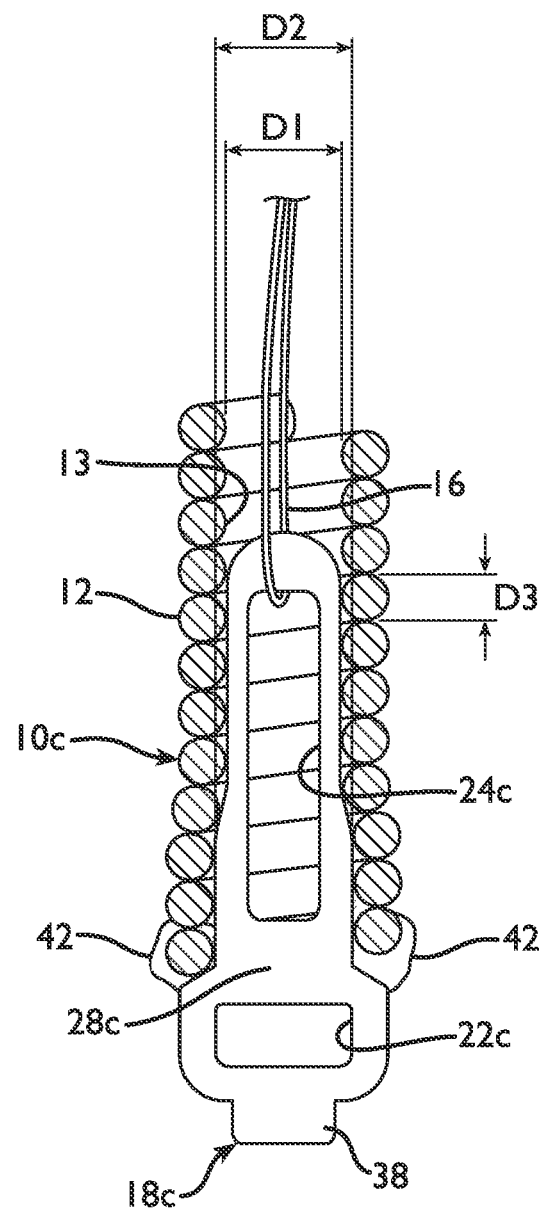
FIG. 15 is an illustration of an end of an embolic implant including a detachment feature expanding an inner diameter of an embolic coil according to aspects of the present invention.

FIG. 15 is a cross sectional illustration of a proximal section of an alternatively constructed implant 10c having elements as described in relation to FIG. 1A with like reference numbers indicating like elements. Compared to the implant 10a illustrated in FIG. 1A, the implant 10c illustrated in FIG. 15 can have an alternative detachment feature 18c. The detachment feature 18c illustrated in FIG. 18c can have a portion with a width D2 sized to fit within a lumen 13 of an embolic coil 12 having an inner diameter D1. The width D2 of the detachment feature 18c can be larger than the inner diameter D1 of the coil lumen 13 so that when the detachment feature 18c is positioned within the lumen 13, a proximal portion of the lumen 13 expands to a diameter D2 to accommodate the width D2 of the detachment feature 18c. Configured thusly, the expanded portion of the coil 12 can provide a compressive force against the section of the detachment feature having width D2 to help secure the detachment feature 18c to the coil 12.

Compared to the implant 10a illustrated in FIG. 1A, the bridge 28c can extend proximally from a proximal end of the embolic coil 12. Configured thusly, in some configurations, the pull wire 140 need not be inserted into the lumen 13 of the embolic coil 12 to be supported by the bridge 28c. Limiting the length of pull wire 140 that is inserted into the embolic coil 12 can increase the flexibility of the proximal section of the embolic coil.

The implant 10c illustrated in FIG. 15 can be constructed according to the principles illustrated in FIGS. 2A and 2B through FIG. 7. The implant 10c illustrated in FIG. 15 can be used according to the principles illustrated in FIGS. 9 and 11 through 14D.

Figure 16:
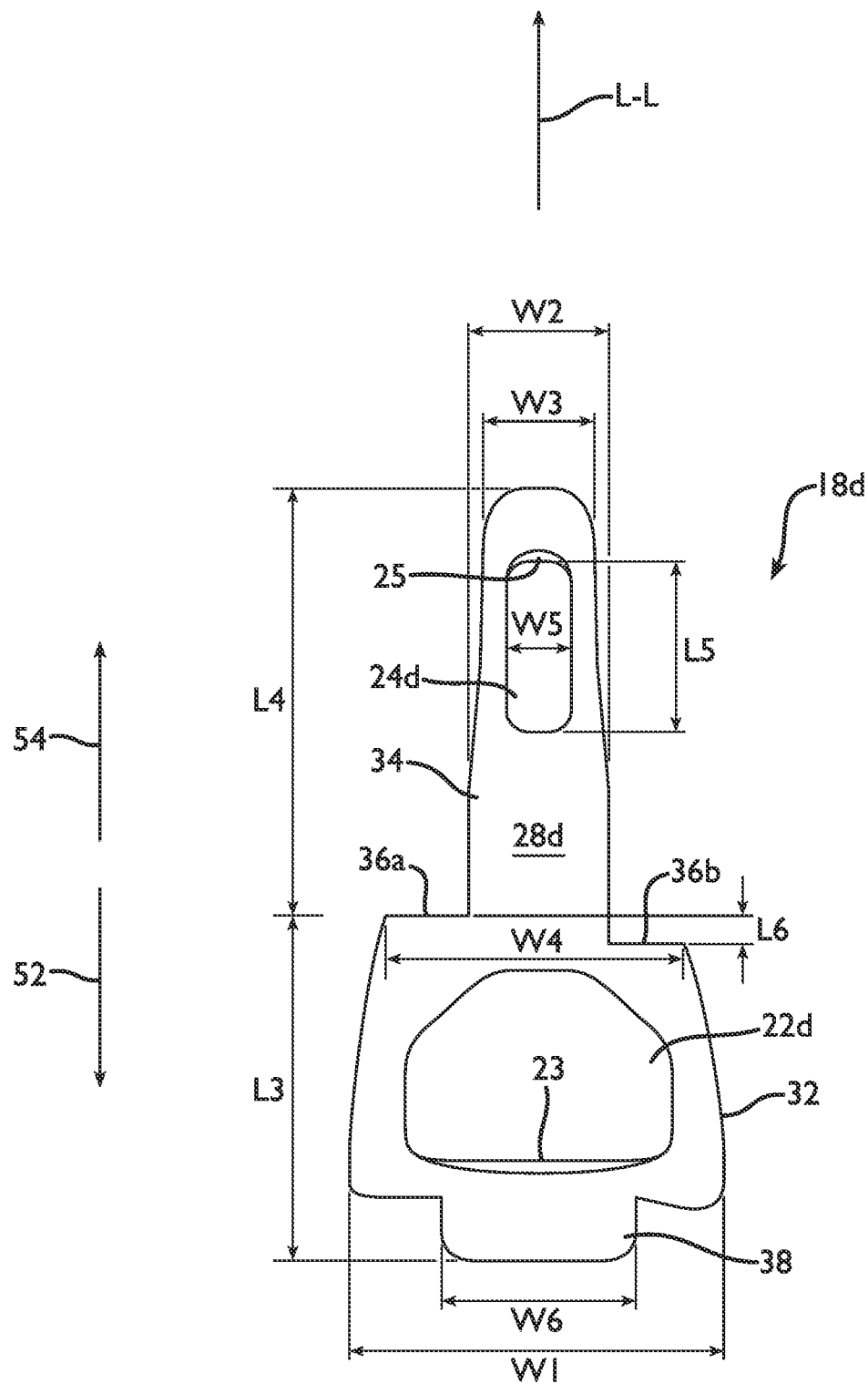
FIG. 16 is an illustration of another example detachment feature according to aspects of the present invention.
Figure 17A:
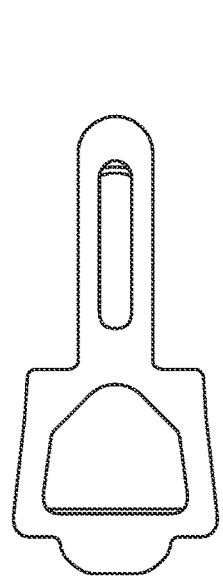
FIGS. 17A through 17H are illustrations of example detachment features according to aspects of the present invention.
Figure 17B:
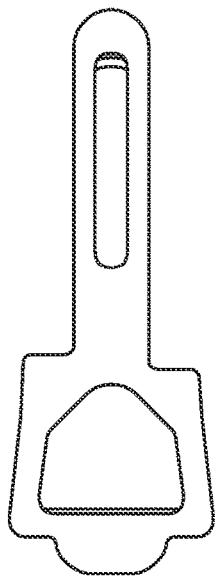
Figure 17C:
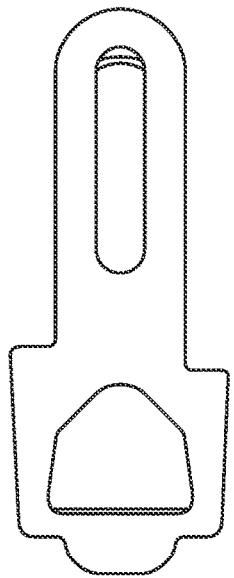
Figure 17D:
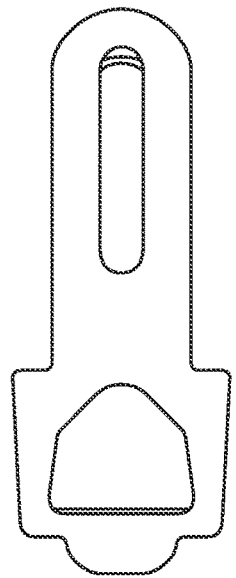
Figure 17E:
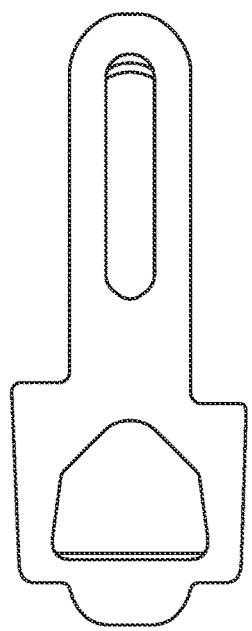
Figure 17F:
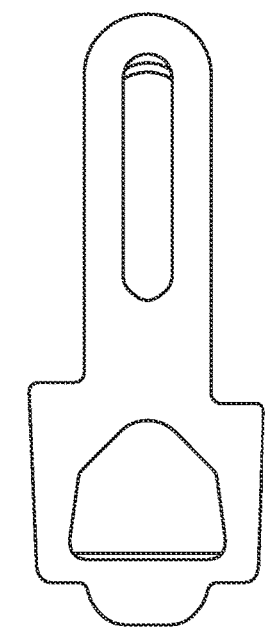
Figure 17G:
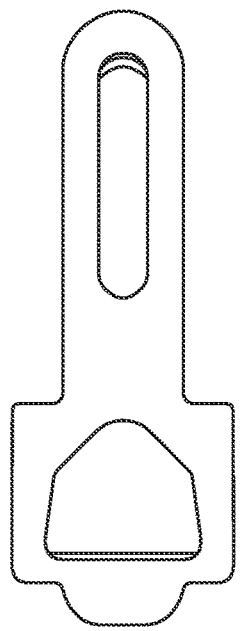
Figure 17H:
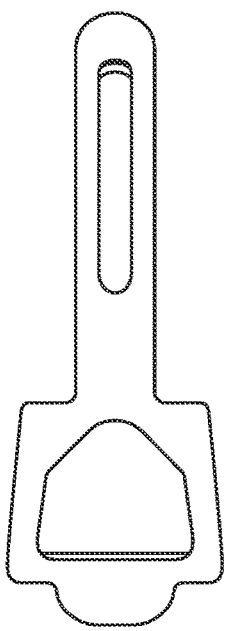

FIG. 16 is an illustration of another example detachment feature 18d. Various dimensions of the detachment feature 18d are illustrated in FIG. 16. The dimensions can be selected based on design criteria, so that the detachment feature 18d can be customized for a given implant. FIGS. 17A through 17H are illustrations of example detachment features having a similar general structure of the detachment feature 18d illustrated in FIG. 16 with the various dimensions illustrated in FIG. 16 adjusted to customize the detachment feature 18d. The detachment feature is oriented in relation to a longitudinal axis L-L, a distal direction 54, and a proximal direction 52.

The proximal portion 32 of the detachment feature 18d has a first width W1 near a proximal end of the detachment feature 18d that is sized to fit within notches 310 of the delivery tube 300. The first width W1 is preferably sized approximately equal to an outer diameter of the distal end 304 of the delivery tube 300.

The distal portion 34 of the detachment feature 18d has a second width W2 and a third width W3 similar to as disclosed in relation to FIGS. 2A and 15.

The proximal portion 32 of the detachment feature 18d has a fourth width W4 near engagement surfaces 36a, 36b of the detachment feature 18d. The fourth width W4 is preferably sized approximately equal to an outer diameter of the embolic coil 12.

A distal opening 24d of the detachment feature 18d has a fifth width W5. The fifth width W5 is sufficiently wide to allow insertion of the stretch resistant fiber 16 and narrow enough to allow for sufficient material of the distal portion 34 of the detachment feature 18d to maintain structural integrity.

The proximal extension 38 of the detachment feature 18d has a sixth width W6. The sixth width W6 is preferably sized about equal to, and less than a diameter of the lumen of the delivery tube 300 at the distal end 304 of the delivery tube 300.

The proximal portion 32 of the detachment feature 18d has a third length L3. The third length L3 is preferably sized about equal to, and greater than a depth of the notches 310 of the delivery tube 300.

The distal portion 34 of the detachment feature 18d has a fourth length L4. The fourth length L4 is preferably sized sufficiently long enough to facilitate assembly of the implant 10, maintain structural integrity of the implant 10, and provide sufficient material for the distal opening 24d and bridge 28d. The fourth length L4 is preferably sufficiently short to allow for flexibility of the proximal portion of the implant 10.

A distal opening 24d of the detachment feature 18d has a fifth length L5. The fifth length L5 is sufficiently long to allow insertion of the stretch resistant fiber 16 and short enough so that the fourth length L4 can be sufficiently short.

The detachment feature 18d can include a longitudinal offset between engagement surfaces 36a, 36b. The longitudinal offset (sixth length L6) is preferably sized approximately equal to one half a diameter D3 (FIG. 15) of the wire which winds to make the embolic coil 12.

The distal opening 24d can include an atraumatic surface 25 in contact with the stretch resistant fiber when the implant 10 is assembled. The atraumatic surface 25 can be shaped to reduce likelihood of abrasion of the stretch resistant fiber 16 by the detachment feature 18d. Likewise, the proximal opening 22d can include an atraumatic surface 23 shaped to reduce likelihood of abrasion of the loop wire 400 by the detachment feature 18d.

Figure 18:
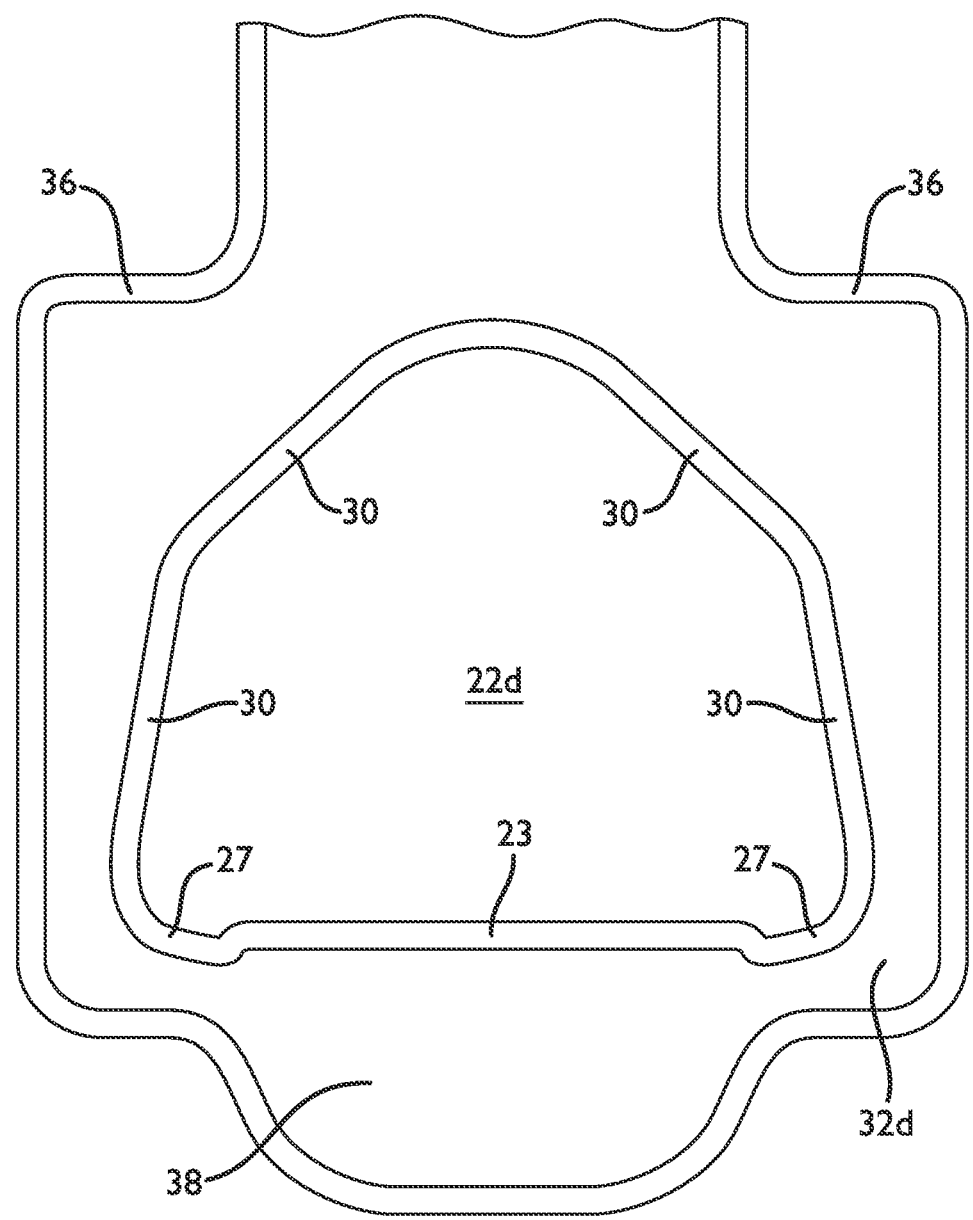
FIG. 18 is an illustration of a proximal portion of the example detachment feature illustrated in FIG. 16 according at aspects of the present invention.

FIG. 18 is an illustration of the proximal portion 32d of the example detachment feature 18d illustrated in FIG. 16. The proximal opening 22d is approximately a five sided polygon with a base having the atraumatic surface 23 and four, distally extending sides 30 which are approximately equal in length. Corners of the polygon are rounded. Corners 27 adjacent to the atraumatic surface 23 (polygon base) can be deepened to encourage the loop wire 400 to rest in the deepened corners 27.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

The descriptions contained herein are examples of embodiments of the invention and are not intended in any way to limit the scope of the invention. As described herein, the invention contemplates many variations and modifications of the implant and methods for making and using the same, including alternative materials, alternative geometries of component parts, alternative positioning of component parts in relation to each other, etc. These modifications would be apparent to those having ordinary skill in the art to which this invention relates and are intended to be within the scope of the claims which follow.

What is claimed is:

1. An embolic implant comprising:
an embolic coil comprising a coiled wire;
a detachment feature affixed to the embolic coil approximate a proximal end of the embolic coil, the detachment feature comprising a first engagement surface and a second engagement surface longitudinally offset from each other by a length approximately equal to half of a diameter of the coiled wire; and
a stretch resistant fiber engaged to the detachment feature, extended through a lumen of the embolic coil, and affixed to the embolic coil approximate a distal end of the embolic coil,
wherein the detachment feature comprises a first opening therethrough and a second opening therethrough separated from the first opening,
wherein the stretch resistant fiber passes through the first opening,
wherein at least a portion of the first opening is positioned within the lumen of the embolic coil,
wherein at least a portion of the second opening is positioned proximally from the proximal end of the embolic coil, and
wherein the second opening comprises an approximately polygon shape comprising four sides of approximately equal length and a fifth side of greater length than the four sides, the fifth side being orthogonal to a longitudinal axis of the detachment feature.

2. The embolic implant of claim 1, wherein the stretch resistant fiber is effective to limit separation of windings of the embolic coil as the embolic coil is reshaped.

3. The embolic implant of claim 1, wherein the second opening comprises an atraumatic surface at a distal end of the second opening.

4. The embolic implant of claim 1, wherein the first opening comprises an atraumatic surface orthogonal to the longitudinal axis of the detachment feature.

5. The embolic implant of claim 1, wherein the approximately polygon shape comprises two corners on either end of the fifth side that are each respectively extended in a proximal direction in relation to the fifth side.

6. The embolic implant of claim 1,
wherein the lumen of the embolic coil comprises an inner diameter,
wherein the detachment feature comprises a proximal portion disposed proximally from the lumen and a distal portion disposed within the lumen,
wherein the proximal portion comprises a first width measuring greater than the inner diameter of the lumen, and
wherein the distal portion comprises a second width measuring about equal to the inner diameter of the lumen.

7. A system comprising:
an implant comprising an embolic coil and a detachment feature, the detachment feature comprising a distal portion extended within a lumen of the embolic coil, a proximal portion extending proximally from a proximal end of the embolic coil, a first engagement surface affixed to the proximal end of the embolic coil, and a second engagement surface affixed to the proximal end of the embolic coil, the first engagement surface and the second engagement surface being longitudinally offset from each other by a length approximately equal to half a diameter of a coiled wire of the embolic coil;
a pull wire;
a delivery tube attached to the detachment feature and configured to detach from the implant upon proximal translation of the pull wire; and
a loop wire affixed to the delivery tube,
wherein the detachment feature further comprises a proximal opening through the proximal portion,
wherein the loop wire is extended through the proximal opening and around the pull wire so that the delivery tube is attached to the detachment feature,
wherein the proximal opening comprises an atraumatic surface apposed to the loop wire,
wherein the atraumatic surface comprises two deepened corners each respectively extended in a proximal direction in relation to a side of the atraumatic opening that is orthogonal to a longitudinal axis of the detachment feature, and
wherein the loop wire is positioned within each of the two deepened corners.

8. The system of claim 7, wherein the detachment feature further comprises a distal opening through the distal portion, and
wherein the implant further comprises a stretch resistant fiber extending through the distal opening and affixed to the embolic coil approximate a distal end of the embolic coil.

9. The system of claim 8, wherein the distal opening comprises an atraumatic surface apposed to the stretch resistant fiber.

10. The system of claim 8, wherein the stretch resistant fiber is effective to limit separation of windings of the embolic coil as the embolic coil is reshaped.

11. The system of claim 7, wherein the proximal opening is shaped to approximate a five sided polygon.

12. The system of claim 7,
wherein the detachment feature further comprises a distal opening through the distal portion,
wherein the detachment feature further comprises a bridge separating the distal opening and the proximal opening, and
wherein the bridge supports a portion of the pull wire.

13. The system of claim 7, wherein the proximal portion of the detachment feature comprises a width approximately equal to an outer diameter of the delivery tube.

14. The system of claim 7, wherein the proximal portion of the detachment feature comprises a width approximately equal to an outer diameter of the embolic coil.

15. The system of claim 7, wherein the proximal portion comprises a proximal extension comprising a width less than and approximately equal to a diameter of a lumen of the delivery tube at a distal end of the delivery tube.

* * * * *